(12) United States Patent
Björkesten

(10) Patent No.: US 6,260,034 B1
(45) Date of Patent: Jul. 10, 2001

(54) METHOD AND A SYSTEM FOR NUCLEIC ACID SEQUENCE ANALYSIS

(75) Inventor: Lennart Björkesten, Storvreta (SE)

(73) Assignee: Amersham Pharmacia Biotech AB, Uppsala (SE)

( * ) Notice: Subject to any disclaimer, the term of this patent is extended or adjusted under 35 U.S.C. 154(b) by 0 days.

(21) Appl. No.: 09/424,518

(22) PCT Filed: May 27, 1998

(86) PCT No.: PCT/SE98/01005

§ 371 Date: Nov. 23, 1999

§ 102(e) Date: Nov. 23, 1999

(87) PCT Pub. No.: WO98/54669

PCT Pub. Date: Dec. 3, 1998

(30) Foreign Application Priority Data

May 28, 1997 (SE) .................................................. 9702008

(51) Int. Cl.[7] .............................. G06F 17/00; G01N 31/00
(52) U.S. Cl. .................................. 706/47; 702/27; 706/45
(58) Field of Search .............................. 364/497, 413.01, 364/413.07; 395/924; 702/27; 706/45, 47

(56) References Cited

U.S. PATENT DOCUMENTS 5,365,455   11/1994   Tibbetts et al. ...................... 364/497
5,502,773    3/1996   Tibbetts et al. ...................... 382/129

FOREIGN PATENT DOCUMENTS

WO 97/02488   1/1997   (WO) .

OTHER PUBLICATIONS

Andersson, P., International Search Report; Aug. 11, 1998; International Application No. PCT/SE98/01005; pp. 1–2.

*Primary Examiner*—John S. Brusca
*Assistant Examiner*—Young Kim
(74) *Attorney, Agent, or Firm*—Jenkens & Gilchrist, P.C.

(57) ABSTRACT

A method and a system for identifying mutations within nucleic acid sequences. Using raw data signals from conventional nucleic acid sequencing equipment, a method to create input signals that enables a properly trained neural network to output a mutation/no mutation signal is provided. Further, an instrument system to perform the method is provided.

15 Claims, 5 Drawing Sheets

METHOD AND A SYSTEM FOR NUCLEIC ACID SEQUENCE ANALYSIS

TECHNICAL FIELD OF THE INVENTION

The present invention relates to the study of nucleic acid sequences in order to determine the occurrence of mutations, i.e. deviations from the anticipated, normal nucleic acid sequence, and more particularly to a method and a system for determination of point mutations, i.e. single nucleotide replacement within otherwise intact portions of nucleic acid sequences.

BACKGROUND OF THE INVENTION

A nucleic acid sequence is usually determined with a combination of conventional electrophoresis and chemical methods to label and identify individual nucleotides. Such methods, like the Maxam-Gilbert method or the Sanger method, are used to determine the order of nucleotides in a nucleic acid sequence.

The determined nucleic acid sequences may be studied for various reasons. One important area is to analyze the nucleic acid sequences with respect to the possible presence of mutations.

Mutation analysis has many applications. A typical case is to analyze a sample extracted from a group of cells from a tumor in order to identify mutations that indicate the presence of cancerous growth. Other cases include investigations to determine the presence of mutations inherited from the male and/or female parent.

A method to determine mutations includes the steps of:
i) electrophoresis separation of a prepared sample and monitoring, for example, the fluorescence activity of certain labeled components added to the sample and converting these fluorescence activities to electrical signals;
ii) identification of signals as representing nucleotide sequences, for example by using specific software;
iii) alignment of the sample nucleotide sequence with respect to a reference sequence wherein the nucleotide sequence is known and wherein further each nucleotide is associated with a position number, in order to assign proper position numbers to the nucleotides of the sample sequence;
iv) identification of sequence positions where deviations between the sample and the reference sequence occur, and, where said deviations indicate potential mutations;
v) a close manual examination of raw data for all identified potential mutations and a subsequent classification of the positions investigated as "mutations" or "non mutations".

Step i) above may be performed manually with relatively simple equipment or by highly automated instruments, such as the Pharmacia Biotech ALFexpress equipment (Pharmacia Biotech, Sweden).

The evaluation according to step ii) is also known as "base calling". It is done manually or preferably by computerized algorithms, often included in an automated equipment used in step i). Such algorithms typically have certain features in the signals, such as local minimum or maximum intensities, as input and then provide output in the form of nucleotide sequences, such as "CCTGAAGCTC", (as shown in SEQ ID NO:1) where the letters A, C, G, and T designates the purine base adenine, the pyrimidine base cytosine, the purine base guanine, and pyrimidine base thymine, respectively.

The output is normally presented as printouts or binary files.

However, the raw data signals from the nucleic acid sequencing equipment contain disturbances, for example originating from fluctuations in the properties of the separation media used, e.g. an electrophoresis gel, or anomalies originating from the previous steps of preparing the sample. Such disturbances may cause the algorithms to interpret the signals in a wrong way, and consequently indicate false mutations or hide a mutation by incorrectly indicating the expected nucleotide.

Methods for reducing such incorrect interpretations have been suggested. For example, Tibbetts et al have in U.S. Pat. Nos. 5,365,455 and 5,502,773 disclosed the use of neural networks for automatic nucleic acid sequence determination to significantly reduce the misinterpretation rates, wherein a neural network is fed with information from the neighboring nucleotides in order to achieve a very high base calling accuracy.

Steps iii) and iv) above refer to a simple comparison and correlation between the sample sequence and the reference sequence. As is well known in the art, this step is well suited for automation.

Step v) is performed manually by a specially trained operator, since reliable automated methods, hitherto, have not been present.

The conventional manual procedure to classify the deviating nucleotide position as true mutation or false indication, according to step v) above, presents problems.

The graphs obtained when measuring the fluorescence signals suffer from normal variations due to disturbances in the raw signals, as described above. This and other factors, such as coexistence of both mutated and non mutated polynucleotides within a sample, tend to make the raw data ambiguous and consequently the interpretation becomes difficult.

The interpretation will therefore depend on the skill and experience of the examiner, which means that the decision between "mutation" or "non mutation" may differ between different examiners.

Furthermore, the manual examination is a time consuming and tedious task. There is therefore a considerable risk that a tired examiner may misinterpret the data.

SUMMARY OF THE INVENTION

The present invention sets out to facilitate the classification of single nucleotide positions within nucleic acid sequences, with respect to the presence or absence of mutations.

This is achieved in one aspect of the invention by a method, as defined in claim 1, by utilizing a trainable neural network for analyzing specific nucleotide positions of the nucleic acid sequences.

It another aspect of the invention there is provided a system of instruments for implementation of the method according to the invention, as claimed in claim 12.

Embodiments of the invention are defined in the dependent claims.

According to the invention, an input pattern representing characteristics for a single nucleotide position in a sequence to be analyzed is used as input to a neural network. The neural network thereby responds with an output signal representing the mutation status.

The input pattern is determined by calculating characteristic values for a number of properties associated with the raw data signals for said nucleotide position, as well as from a corresponding reference sequence. The raw data signals are generated by a suitable conventional technique, such as electrophoresis.

In a training phase, the output signal is used to update the neural network until it is able to produce an output signal which may be interpreted as characteristic for either a mutated or a non-mutated sample sequence.

In an analysis phase the trained neural network is used to classify sample sequences of completely or partly unknown mutation status.

DETAILED DESCRIPTION OF A PREFERRED EMBODIMENT

The method according to the present invention will be described by way of an example, with reference to the attached drawings, whereby the example also constitutes a preferred embodiment.

The expression "sample sequence" as used herein refers to a nucleic acid sequence, such as a DNA or a RNA sequence, from a sample of biological tissue or synthesized sequences, said sequence determined with any conventional method that produces raw data signals for the separate nucleotide bases and interpreted as a sequence of nucleotide bases. The sample sequence may be of arbitrary length, although a minimum length of 25 through 50 base pairs is preferred in order to achieve reliable results.

Similarly, "reference sequence" refers to a nucleic acid sequence of generally the same portion of a nucleic acid strand as the corresponding sample sequence, and with a corresponding set of raw data achieved by the same method as the sample sequence, but regarded as having a known set of nucleotide bases at known nucleotide positions.

Figure 1:
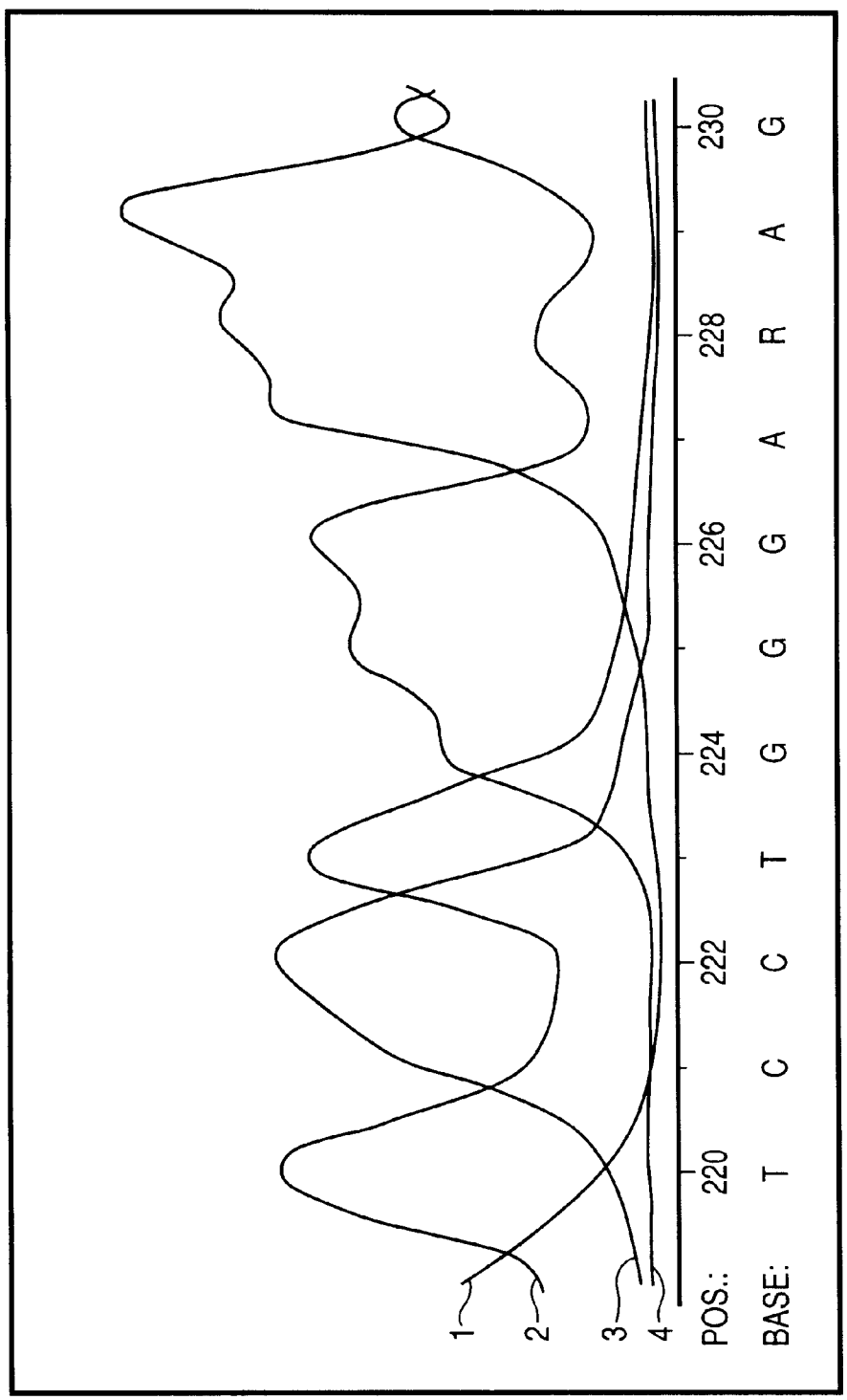
FIG. 1 is an output diagram from an automated base calling equipment, showing raw data signals and the associated interpreted nucleotide sequence of a part of a nucleic acid sequence.

FIG. 1 illustrates the raw data representing a sample nucleic acid sequence, in this case a DNA sequence, as received after a conventional electrophoresis separation, wherein the separated components have been detected by the use of any conventional method able to generate electrical signals representing intensity levels for a nucleotide base sequence, e.g. detection of light emitted from molecule fragments, representing the respective nucleotides in the sequence, labeled by a fluorescent probe.

The raw data includes four specific graphs 1,2,3,4, each graph representing the detected intensity signal of one of the nucleotide bases A, C, G, T, respectively. In the example of FIG. 1, graph 1 represents detection of base A, graph 2 represents base T, graph 3 represents base C, and graph 4 represents base G.

FIG. 1 also illustrates the nucleotide sequence derived from the intensity signals during base calling, e.g. by utilizing a conventional base calling software.

Further, position numbers for each nucleotide base ranging from 220 through 230 have been added after alignment of the sample sequence with respect to a reference sequence with known position numbers.

As can be noted, the nucleotide position 228 is marked with the letter R. This is to indicate that the determination of the nucleotide on position 228 has been found to be uncertain.

Such uncertainty may have arisen due to a number of reasons. For example, the base calling software may not have been able to interpret the local values of the intensity signals as a specific nucleotide base. The uncertainty may also have been detected during alignment if a determined nucleotide base differs from what is expected with respect to the reference sequence.

There is therefore a need to determine if the uncertain position actually holds a mutation, or if it holds the expected nucleotide base although its raw signals for some reason have been disturbed.

It should be noted that the graphs of FIG. 1 could also serve as an example of a reference sequence, although a reference sequence does not include indications of uncertain nucleotides. Of course, the graphs of a reference sequence also differ slightly from the graphs of a corresponding sample sequence in all positions, certain as well as uncertain, due to a number of reasons such as variations in purity and pretreatment before the base separation.

According to the invention, a neural network is used to evaluate the information present in the raw data signals of the sample and the reference sequences.

The theoretical background to neural networks may be obtained from, for example, "Neural Networks—A Comprehensive Foundation", S. Haykin, 1994, Prentice Hall, which is hereby incorporated by reference herein. The fundamental concept of neural networks, is disclosed on p. 1–41 of the reference.

Figure 5:
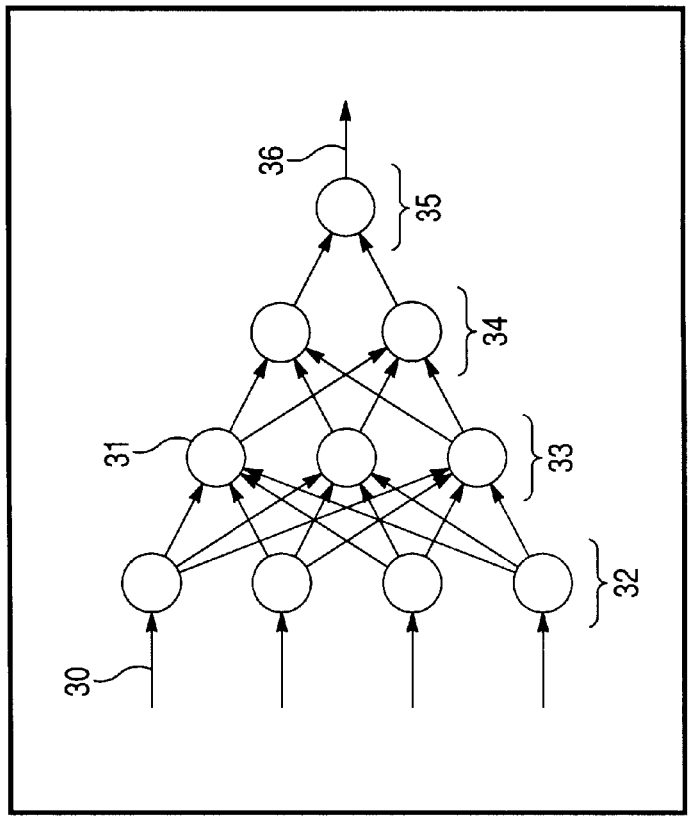
FIG. 5 is a diagram illustrating a typical neural network.

FIG. 5 shows, for illustrative purpose, an example of a neural network, wherein the network includes four input lines 30, one output line 36 and four layers of neurons 31. An input layer 32 comprises four neurons, a first hidden layer 33 comprises three neurons, a second hidden layer 34 comprises two neurons and an output layer 35 comprises an output neuron. The neural network shown in FIG. 5 is an example of a fully connected neural network, since all neurons in one layer are connected to all neurons in the next layer downstream.

The simplified neural network of FIG. 5, which has been selected to give a clear and easy-to-read illustration of some of the components of a neural network, is not identical with the neural network utilized in the described embodiment of the present invention.

The neural network of the embodiment is instead defined in Table I.

TABEL I

Definition of neural network according to an embodiment of the invention. Refer to the Haykin reference for explanation of terms.
Multilayer, fully connected, feedforward network

| Layer | Number of neurons | Step | Momentum |
|---|---|---|---|
| Input | 16 | 1.0 | 0.5 |
| Layer 1 | 7 | 0.5 | 0.5 |
| Layer 2 | 4 | 0.1 | 0.5 |
| Output | 1 | — | — |

| Sigmoid type activation function: | $\tanh(k*x(i) + m(i))$ |
|---|---|
| Output range: | −1 through +1 |

The neural network of the embodiment, as defined in Table I, is a conventional multilayer perceptron. For a more thorough understanding of multilayer perceptrons and the associated technical terms, see the above Haykin reference p. 106–120 and p. 138–185.

The neural network may be implemented as an electronic hardware equipment. However, it is preferred to implement it by using a commercially available neural network emulator of conventional type, like NeuroSolutions which is available from NeuroDimension, Inc., Gainesville, USA.

A neural network needs to be provided with input in the form of a set of input signals. Such a set of input signals, required to produce an output signal, is herein referred to as an input pattern.

According to the invention, input patterns are derived from raw signal data related to individual nucleotide positions of sample sequences and corresponding reference sequences. The input patterns are so designed that they contain information enough to enable the neural network to classify differences between the sample raw data and the reference raw data as mutations or non-mutations, provided that the network has previously been trained with input patterns of known status.

An illustrative example of an embodiment of such an input pattern shall now be described in detail.

According to this embodiment, the input pattern is derived from a selected set of property values for three different properties associated with the intensity levels of each raw data signal, i.e. the respective signal for each of the four base nucleotides abbreviated A, C, G, and T, at each respective nucleotide position. "Property value" is herein abbreviated as PV.

The three properties, which according to the embodiment have been identified to contain essential information of the intensity signals are called the peak amplitude property, the modulation amplitude property and the asymmetry property.

The peak amplitude PV is defined as the intensity value at the analyzed nucleotide position.

Figure 2:
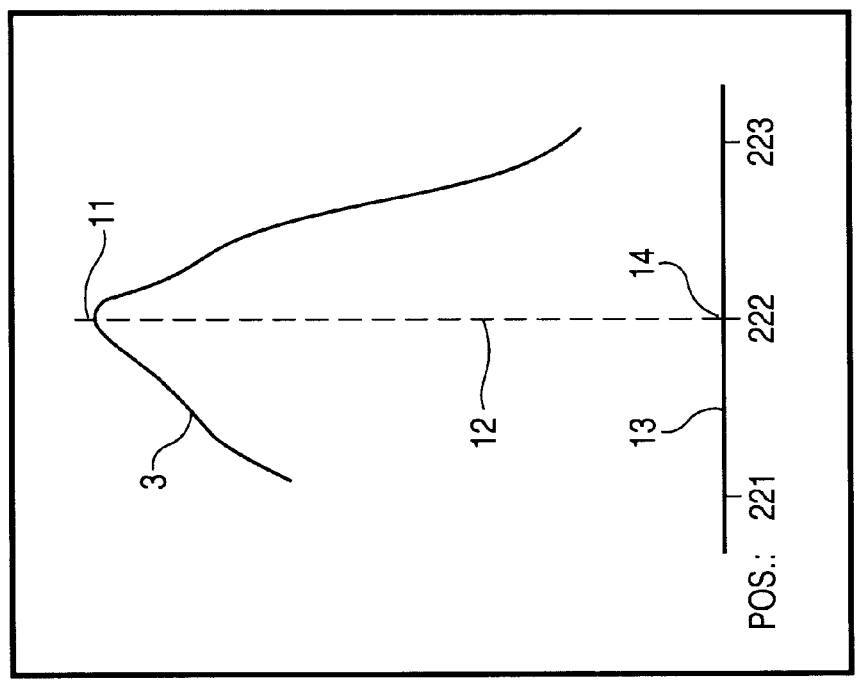
FIG. 2 is a diagram showing a portion of a graph according to FIG. 1, in which the calculation of the peak amplitude property is illustrated.

FIG. 2 shows the principle of graphically determining the peak amplitude PV for one graph of one nucleotide position. The illustrated graph is a portion in the vicinity of position 222 of the intensity signal graph 3 for the C base of FIG. 1. Position 222 has, for illustrating purpose, been selected as the analyzed position even though, as can be understood of FIG. 1, that position was not assessed to be a uncertain position during the base calling.

The peak amplitude PV is graphically determined as the signal intensity level at the point of intersection 11 between the graph 3 and a line 12 drawn perpendicularly to the base line 13 and intersecting the base line at the position indication mark 14 for the analyzed position.

In the present embodiment, the peak amplitude PV is determined in the same way for each graph at each analyzed position. This means that each nucleotide position is associated with four peak amplitude PV's, one for each nucleotide base type.

The modulation amplitude PV is defined as the peak amplitude PV minus the mean value of the signal intensity levels determined half a nucleotide position upstream and downstream, respectively, with respect to the analyzed nucleotide position.

Figure 3:
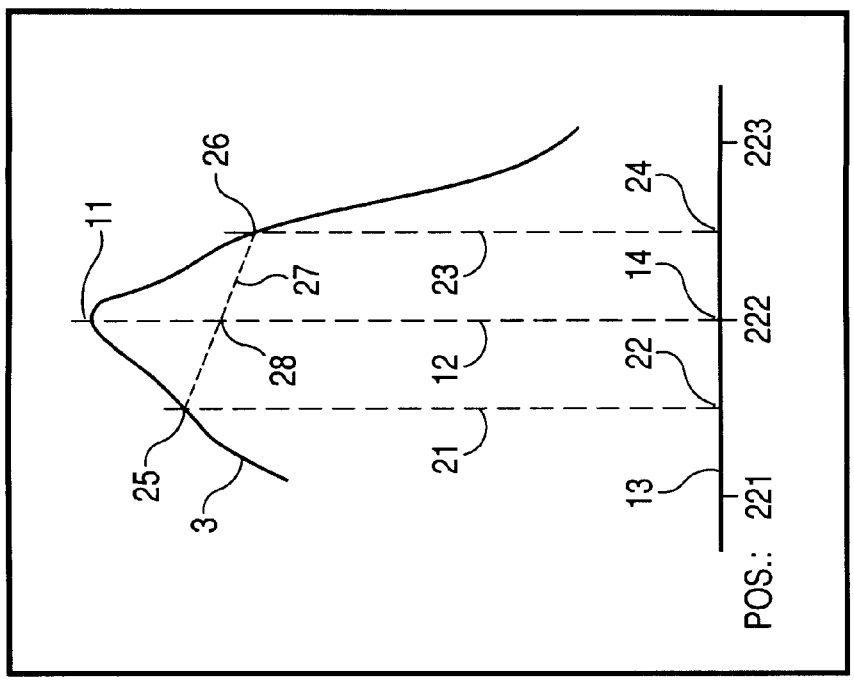
FIG. 3 is a diagram showing a portion of a graph according to FIG. 1, in which the calculation of the modulation amplitude property is illustrated.

FIG. 3 shows the principle of graphically determining the modulation amplitude PV for one graph of one nucleotide position. The illustrated graph is the same portion, with the same analyzed position, as in FIG. 2.

A first line 21 is drawn perpendicularly to the base line 13, intersecting the baseline at a point 22 spaced half a nucleotide position to the left of the analyzed position. Similarly, a second line 23 is drawn perpendicularly to the base line 13, intersecting the baseline at point 24 spaced half a nucleotide position to the right of the position to be analyzed.

Both the first and the second lines 21, 23 are extended until they intersect the graph 3 at points 25 and 26 respectively. A third line 27 is drawn through the intersection points 25, 26.

A fourth line 12 is drawn perpendicularly to the base line 13, in such a way that it intersects the base line 13 at a point 14 representing the position to be analyzed, and also so that it intersects the graph 3 and the third line 27 at points 11 and 28, respectively.

The modulation amplitude PV is graphically determined as the intensity value at the point 11, where the line 12 intersects the graph 3 minus the intensity value at the point 28 where the line 27 intersects the line 12.

The modulation amplitude PV is determined in the same way for each graph at each analyzed position. This means that each nucleotide position is associated with four modulation amplitude PV's, one for each nucleotide base type.

The asymmetry PV is defined as the signal intensity level half a nucleotide position upstream of the analyzed position minus the signal intensity level half a nucleotide position downstream of the analyzed position.

Figure 4:
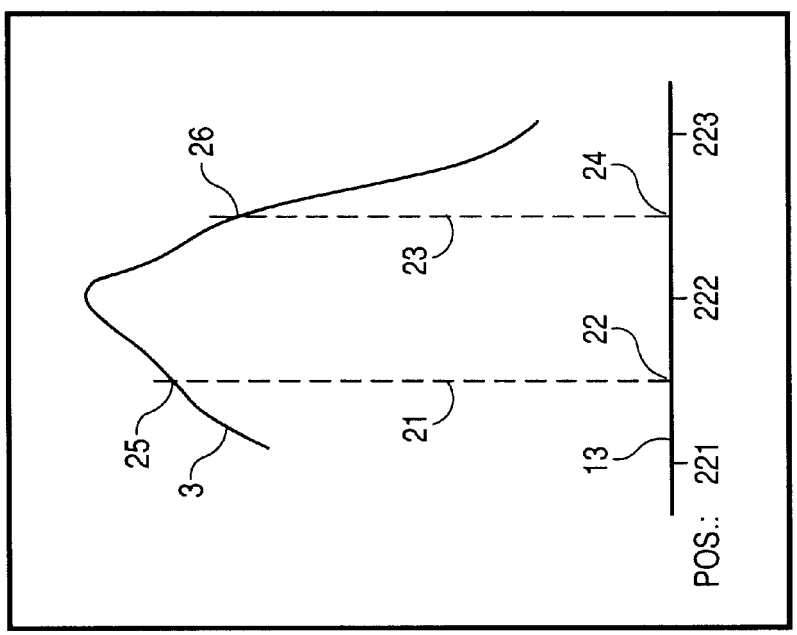
FIG. 4 is a diagram showing a portion of a graph according to FIG. 1, in which the calculation of the asymmetry property is illustrated.

FIG. 4 shows the principle of graphically determining the asymmetry PV for one graph of one nucleotide position. The illustrated graph is the same portion, with the same analyzed position, as in FIG. 2.

A first line 21 is drawn perpendicularly to the base line 13, intersecting the baseline at a point 22 spaced a half position to the left of the position to be analyzed. Similarly, a second line 23 is drawn perpendicularly to the base line 13, intersecting the baseline at a point 24 spaced a half position to the right of the position to be analyzed.

Both the first and the second lines 21, 23 are extended until they intersect the graph 3 at points 25 and 26, respectively.

The asymmetry PV is graphically determined as the intensity level at the point 26, minus the intensity level at the point 25.

The asymmetry PV is determined in the same way for each graph at each analyzed position. This means that each nucleotide position is associated with four asymmetry PV's, one for each nucleotide base type.

Thus, in the manner described above a total of twelve PV's are determined for each position of the sample sequence.

In a completely analogous way twelve PV's are also calculated for each position of the reference sequence.

The raw data signals may include variations in intensity within a sequence, as well as between sample and reference, due to other factors than those primarily attributed to the presence of nucleotides, such as differences in sample concentrations or irregularities in the separation gel.

Therefore, each PV is transformed into a normalized property value (NPV) in a normalization step.

During the normalization step a number of PV's, representing the same property and the same nucleotide base type but from different nucleotide positions in the vicinity of, but excluding, the actual nucleotide position to be analyzed are added to a local sum. A local mean PV of the values included in the local sum is then calculated by simply dividing the local sum with the number of values.

In order to avoid that alternating positive and negative values result in misinterpreted magnitude of the local mean value or even cause a local sum of zero, which should result in an undefined NPV, each PV is added as a positive value. This means that if a PV is negative it is first multiplied with −1 before it is added to the local sum.

Thus, for example, if at an analyzed position the local mean PV for the asymmetry property of the guanine nucleotide base is to be calculated, the guanine asymmetry PV of the analyzed position in itself is not included in the local sum. Further, only the absolute values of guanine asymmetry PV's from those nucleotide positions where the reference sequence indicates the presence of a nucleotide base of the same type as the type of local sum, in this case guanine, are added to the local sum.

Thus, in the normalization procedure for the sample sequence, both the sample sequence and the reference sequence are used.

The local mean PV is calculated as (the local sum)/(the number of PV's in the local sum).

The number of PV's to be included in the local mean PV is essentially arbitrary, although seven PV's have been found to yield successfully normalized values.

Although it is preferred to calculate the local mean PV with values picked essentially symmetrically around the analyzed position, the local sum may be derived in other ways. For example, picking the values from a one-sided interval towards higher position numbers only, as viewed from the analyzed position, have not shown any measurable effect on the precision of the method compared to a symmetrical interval.

The PV of the analyzed nucleotide position, for the specific property and nucleotide base, is then divided with the corresponding local mean PV to produce its normalized property value, NPV, i.e.:

NPV=PV/(local mean PV)

Thus, a NPV is a normalized representation of a PV of the sample sequence, where the normalization is made with regard to a local part of the sample sequence in itself.

It shall of course be understood that in order to determine the NPV's of a certain nucleotide position it is necessary to have available PV's also for so many surrounding positions that it is possible to calculate the necessary local mean PV.

Thus, after the normalization step the previously determined twelve PV's for each nucleotide position in the sample sequence have been transformed to twelve NPV's for each sample sequence nucleotide position.

Further, the PV's of each position of the reference sequence are normalized in the same way as described above, wherein the local sum is created using reference sequence PV's of exactly the same sequence positions, for each property and each nucleotide base type, respectively, as were used when calculating the corresponding local sums of the sample sequence. Thus, twelve NPV's are calculated for any given nucleotide position in the reference sequence.

According to the present embodiment, the input pattern should characterize differences between the sample sequence and the reference sequence. Therefore, for each analyzed nucleotide position characteristic deviation values, CDV's, are determined for each property and nucleotide base type, respectively.

A CDV is defined as a NPV of a sample sequence minus the corresponding NPV of a reference sequence. This means that the CDV is calculated from the NPV's of the same position, property and nucleotide base type from the sample and reference sequence, respectively.

According to the preferred embodiment, each nucleotide position thus is represented by twelve CDV's, i.e. four CDV's for each of the three properties. Further, each CDV is derived from information originating from both the sample sequence and the reference sequence.

The present embodiment is designed to enable the neural network to analyze any nucleotide position, regardless of which nucleotide base it holds, using the same network architecture. The input signals, constituting the input pattern, therefore have to be assigned to the respective input pattern positions in a well defined order.

This order, which is herein called the sorting order, consists of the four nucleotide bases in a determined order, e.g. A-T-G-C. In this embodiment, the sorting order is established by selecting a sorting property among the properties characterizing the raw data signals, and use it to, as described below, determine the sorting order in a well defined way.

Then, the sorting property is used to constitute the nucleotide base order according to which the separate values should be assigned to the input pattern.

The sorting property should preferably be the property that is assessed to be the most significant for the mutation/non mutation decision. In the present embodiment, the peak amplitude property is selected as the sorting property.

The first nucleotide base in the sorting order for an analyzed nucleotide position is the base of the reference sequence on that very position.

The second, third and fourth bases in the sorting order are the remaining nucleotide bases when sorted after their CDV's for the sorting property at the analyzed position, with the nucleotide base of the highest CDV as the second base in the sorting order and the nucleotide base of the lowest CDV as the fourth base in the sorting order.

The input pattern consists of a certain number of input values, or more correctly positions to which values may be assigned. In the present embodiment the number of positions in the input pattern is sixteen, corresponding to sixteen input lines of the neural network.

Thus, the first position of the input pattern represents the input signal to be fed to the first input line of the neural network, the second position of the input pattern represents the input signal to be fed to the second input line of the neural network, and so on for all input lines of the neural network.

The first four positions of the input pattern of the present embodiment holds the four CDV's of the sorting property, i.e. the peak amplitude, assigned to the input pattern in the sorting order.

In the present embodiment, the modulation amplitude property has been assessed to have the second strongest impact on the mutation/non mutation decision (after the peak amplitude property.

Therefore, the second set of values to be added to the input pattern is accordingly the four modulation amplitude CDV's.

Thus, in the present embodiment, positions 5 through 8 of the input pattern are reserved for the four CDV's, one for each nucleotide base, of the modulation amplitude property, entered in the sorting order, i.e. the same nucleotide base order as for the first four positions in the input pattern.

In a completely analogous way CDV's associated with the third property, asymmetry, are entered at positions 9 through 12 of the input pattern, still sorted in the same sorting order as for positions 1 through 4.

Finally, in the present embodiment, the modulation amplitude NPV's are assigned, in the sorting order, to the positions 13 through 16 of the input pattern.

Thus an input pattern for a specific position of a sample sequence holds information originating from both the sample sequence and the reference sequence, sorted in a well defined way.

The principle of the invention, that is illustrated by the embodiment, is to feed a neural network, such as that described, above with a set of generalized signals, such as the input pattern signals, representing essential information about the correlation between the sample sequence and a reference sequence of known composition.

The network may then be trained with samples of known status to recognize such characteristics of the differences and/or similarities between the sample and the reference raw data signals, that the network for each analyzed nucleotide position responds with a signal that can be interpreted as either an indication of a true deviation (mutation) or a true similarity to the reference sequence on that particular position.

In the present embodiment the network is designed to generate an output signal in the range between −1 and +1 in response to the input pattern. This range is essentially arbitrarily selected and may be altered to any suitable range.

In a training phase, the neural network is fed with input patterns originating from sample sequences of known status, i.e. sequences that have been manually examined and classified as mutated or not mutated.

The output signals generated by the neural network are then compared with the target values, i.e. −1 for no mutation and +1 for mutation.

The deviations between generated values and target values are used to generate error signals that are back propagated into the network in order to train the network to correctly interpret the input patterns. The basics of back propagating are described in the Haykin reference p. 44–87 and p. 185–220.

The training continues in an iterative way until the network is assessed, e.g. by cross validation, to be able to distinguish between truly mutated sequences and false indications.

In an analyzing phase, the properly trained neural network is then useable for classifying sample sequences of unknown status.

The method of the analyzing phase is completely analogous to the learning phase, except that no back propagation is performed. Further, instead of comparing the output signal of the neural network to a known status, the output is used to decide between mutation or non-mutation.

The herein described embodiment of the invention was tested to determine its ability to classify DNA sequence nucleotide positions with or without true point mutations. The tests are summarized in Table II.

TABLE II

Test of an embodiment of present invention.

|  | False mutation | True mutation |
|---|---|---|
| Number of analyzed nucleotide positions | | |
| Training set | 975 | 25 |
| Test set | 199 | 5 |
| Rate of correct classification | | |
| Training set (at end of training) | 99.1% | 100% |
| Test set | 98.6% | 100% |

The training set comprised a total of 1000 nucleotide position in a number of DNA sequences, each one in a previous base calling step found to contain potential mutations. A manual examination of these positions resulted in that 975 were classified as false mutations, i.e. these positions did not contain mutations, while 25 positions of the training set were classified as containing true mutations.

In a similar way, a test set of a total of 204 nucleotide positions were manually examined, resulting in that 199 were classified as false mutations while 5 positions of the test set where classified as containing true mutations.

A neural network, according to the embodiment disclosed herein, was fed with input patterns from the training set, and the resulting output signals were back propagated into the network. The classifications were based on the assumption that an output value less than 0.4 indicated "no mutation", while other output values indicated "true mutation".

The network was trained by iteration until it correctly classified 99.1% of the false mutations and 100% of the true mutations. At that point the training was interrupted.

The neural network was then, for the first time, fed with the test set. The network was then able to correctly classify 98.6% of the false mutations and all of the true mutations.

Figure 6:
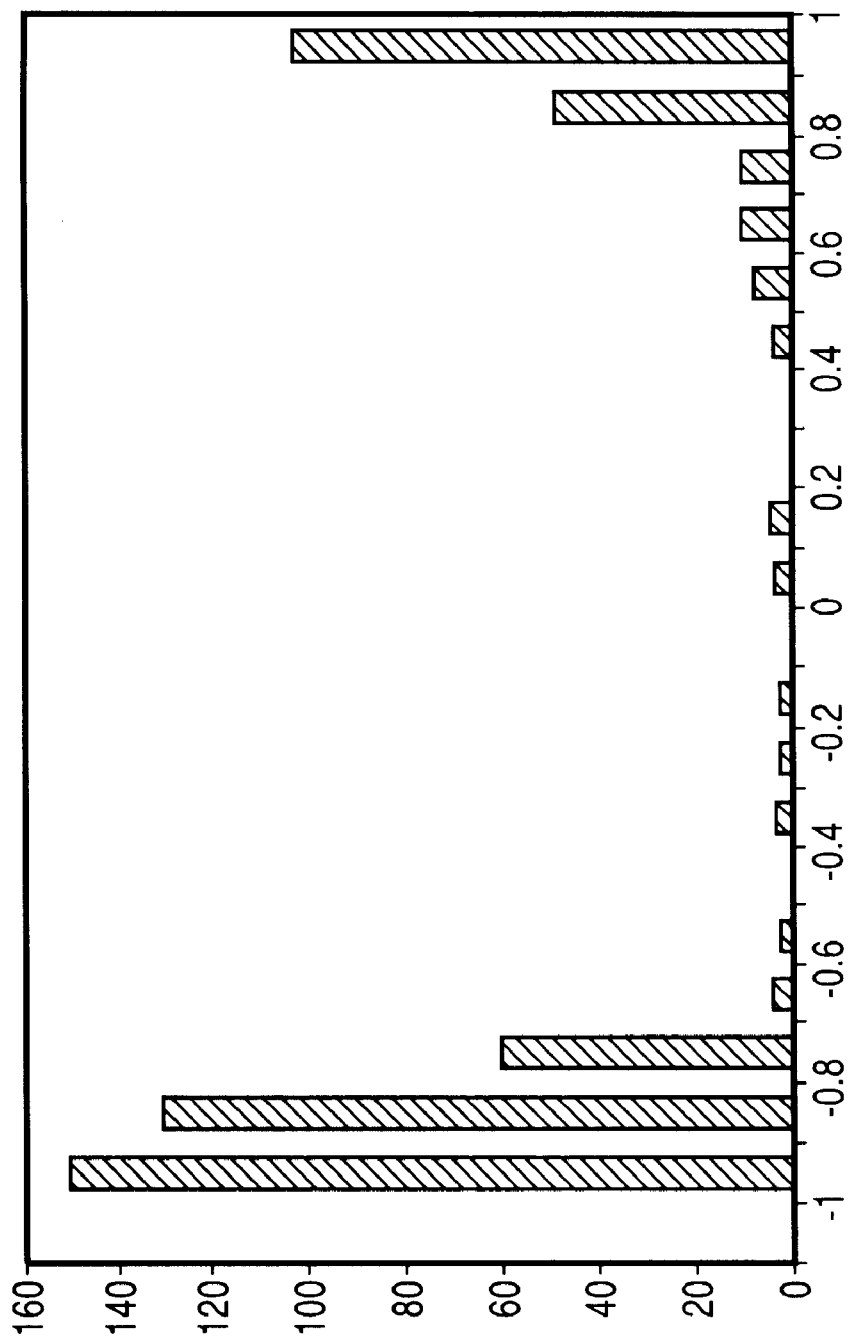
FIG. 6 is a diagram showing a distribution of output signals from a neural network according to the invention.

FIG. 6 shows an illustrative example of a distribution of a number, in this case 528, of output values from a trained neural network, in response to 528 typical input patterns. In FIG. 6, the x-axis represents intervals, in steps of 0.1, of an output signal range of −1 through +1, while the y-axis represents the number of output signals obtained within each interval.

An output value may be transformed to a classification indication by selecting one value within the output signal range to constitute a "border value", like in the previously described test where 0.4 was selected as the border value, and then postulating that an output value higher than the border value represents one mutation class, and an output value lower than the border value represents the other mutation class.

FIG. 6, however, illustrates that although a well designed and properly trained network tends to generate output signals near the extreme ends of the output range, it still in some cases fails to clearly differentiate between mutation/non mutation, by generating an output near the middle of the range.

It is therefore preferred to narrow the ranges for either class to the end regions of the total output value range in order to assure that only the most confident values are classified, leaving a central range of undefined classification.

It is further of interest to estimate the confidence of the classification, i.e. if the neural network generated an output value near any of the extreme ends of the output range thereby indicating that the classification is true with high confidence.

The method of the present invention is well suited for this. Any suitable representation of the relation between the actual output value and the closest extreme value of the output range will serve as an indication of the confidence, ranging from simple subtraction to utilization of any suitable probability calculation.

It shall of course be understood that the example above, constituting a preferred embodiment of the method of the invention, is used for illustrative purpose only, and in no way shall be interpreted as limiting the scope of the invention, which is defined by the scope of the appended claims.

Thus, a number of modifications of the embodiment disclosed above is obvious for anyone skilled in the art, without deviating from the inventive idea of the invention.

Such modifications include different sources for input signals, characteristic properties, calculation methods for property values, choice of input pattern, neural network architecture, etc.

Further, the method according to the invention is not only applicable to nucleic acid sequences containing ambiguous nucleotide positions, but may also be used to routinely check base called sequences. In that way it is possible to detect hidden true mutations, i.e. true mutations that during the base calling incorrectly have been interpreted as in compliance with the reference sequence.

Still further, it is possible to train a neural network with a reference sequence in such a way that the useful information of the reference sequence is present in the internal weights of the network. Thus, in the analysis phase, the user may analyze corresponding nucleic acid sequences without the need to input a reference signal during the analysis.

Figure 7:
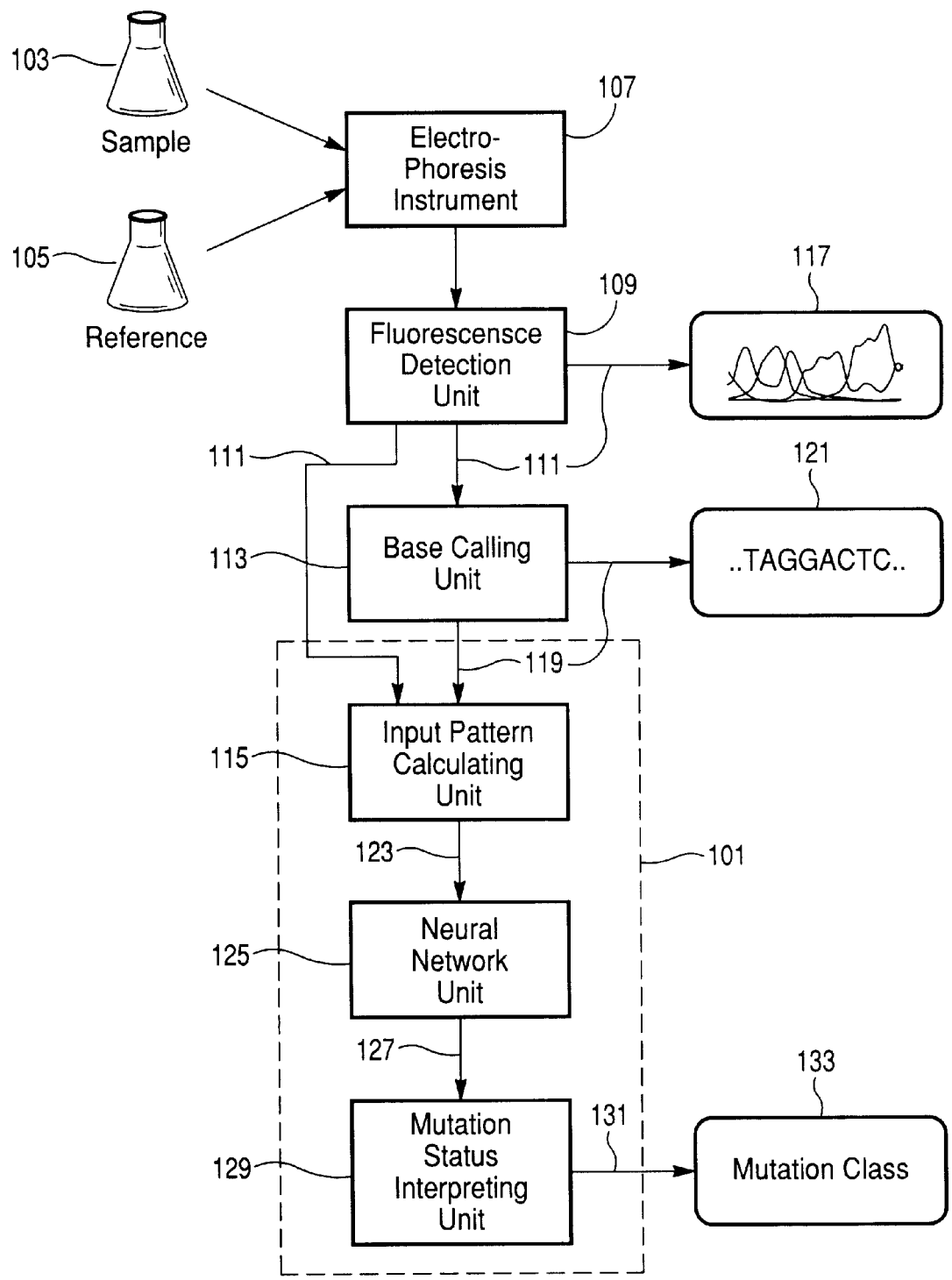
FIG. 7 is a schematic block diagram illustrating a system to practice the method of the invention.

FIG. 7 illustrates components of an instrument system including not only components necessary for practicing the method of the invention, but also including an example of equipment, in this case electrophoresis and fluorescence detecting instruments, to produce the raw data signals to be analyzed using the method of the invention.

In a strict sense, therefore, only an instrument system containing the components within the dashed square 101 of FIG. 7 are necessary to practice the method of the invention, provided that raw data input signals are fed from external sources.

It should be understood that suitable interfaces between the separate components, to adapt them for the transfer of information between the units, are included in the components, respectively.

According to FIG. 7, the sample 103 and reference 105 nucleic acid sequence solutions, properly prepared for the electrophoresis and fluorescence detection, are added to the electrophoresis instrument 107, of conventional design, for separation into detectable components. During or after the separation the separated components are detected by the fluorescence emitted when excited by laser light.

The fluorescence detection unit 109, of any suitable conventional design, produces intensity signals 111, representing the intensity levels of fluorescence for the respective nucleotide bases of the sample and reference sequence, respectively. The intensity signals 111 are output to a base calling unit 113 and an input pattern calculating unit 115, and may also be sent to an output device 117, like a printer.

The conventional base calling unit 113 interprets the intensity signals 111 to sequences of nucleotide bases. Further, the base calling unit 113 may specifically label a position in a sequence that is not determined with sufficiently high confidence. The output signals 119 of the base calling unit 113, preferably in digital form, is forwarded to the input pattern calculating unit 115, and may also be sent to an output device 121, like a printer.

The input pattern calculating unit 115 is fed with the output signals 119 of the base calling unit 113, as well as the intensity signals 111 of the fluorescence detection unit 109.

In the embodiment of the system of the invention, as illustrated in FIG. 7, the intensity signals 111 from the fluorescence detection unit 109, as well as the output 119 from the base calling unit 113, are continuously forwarded to the input pattern calculating unit 115. However, it is equally possible to, by manual action, forward only those signals that represent uncertain nucleotide positions.

The input pattern calculating unit 115 performs the steps of the method of the invention necessary to create an input pattern and outputs, for each nucleotide position to be analyzed, signals 123, constituting an input pattern, to a neural network unit 125 which preferably comprises a neural net such as that defined above in Table I.

The neural network unit 125, when properly trained, outputs a signal 127 within a predetermined range, representing a mutation status classification. This signal 127 is forwarded to a mutation status interpreting unit 129.

The mutation status interpreting unit 129 determines, by using any suitable decision algorithm, if the output signal 127 from the neural network unit 125 represents a mutated nucleotide position, or not. the mutation status interpreting unit 129 may further calculate the confidence of the mutation classification.

The mutation status interpreting unit 129 outputs signals 131 representing the mutation/non mutation decision, as well as the confidence estimate, to an output device 133 such as a monitor screen or a printer.

It should be noted that although FIG. 7 indicates all components of the instrument system as suitably designed hardware equipment, some of the components, like the neural network, may instead be implemented as software in a computer.

What is claimed is:

1. A method for nucleic acid sequence point mutation analysis comprising the steps of:

determining deviations between at least one set of intensity signals representing nucleotide bases in a sample nucleic acid sequence with at least one set of intensity signals from a corresponding reference sequence of predetermined nucleotide composition by comparing said intensity signals at at least one specific nucleotide position; and analyzing said deviations to determine a mutation status of said specific nucleotide position in said sample sequence, characterized in that said analyzing step is performed by feeding a neural network with input signals that represent said deviations, and said neural network having been trained with a number of sample nucleic acid sequences of predetermined mutation status to generate an output signal representing a mutation status classification in response to said input signals.

2. The method according to claim 1, characterized in that said intensity signals represent raw data from an electrophoresis separation originating from a biological sample.

3. The method according to claim 2, characterized in that mutation status is defined as a property characterizing the probability that said specific nucleotide position in the nucleic acid sample sequence holds a nucleotide base different from the nucleotide base present at the corresponding position in the reference sequence.

4. The method as in one of claims 1–3, characterized in that said analyzing step comprises the step of providing, for each specific nucleotide position to be analyzed, the neural network with an input pattern comprising a set of input signals, wherein said input pattern represents deviation values derived from a comparison between property values of the sample sequence and the reference sequence, said property values being associated with at least one property of said intensity signals, and said neural network is responsive to said input pattern for generating an output signal that is representative of the mutation status of said analyzed nucleotide position.

5. The method according to claim 4, characterized in that said at least one property of said intensity signals is selected from a group consisting of:

a peak amplitude property, a modulation amplitude property, and an asymmetry property.

6. The method according to claim 5, characterized in that said peak amplitude property is defined as the intensity signal value at the analyzed nucleotide position.

7. The method according to claim 5, characterized in that said modulation amplitude property is defined as the intensity signal value at the analyzed nucleotide position minus the mean value of the signal intensity level half a nucleotide position upstream and the signal intensity level half a nucleotide position downstream, respectively, of the analyzed position.

8. The method according to claim 5, characterized in that said asymmetry amplitude property for an analyzed position is defined as the signal intensity level half a nucleotide position upstream of the analyzed position minus the signal intensity level half a nucleotide position downstream of the analyzed position.

9. The method according to any of claims 5 through 8, characterized in that the property values for at least one of said properties are normalized to compensate for local variations of intensity signal strength.

10. The method according to claim 9, characterized in that at least one property is selected as a sorting property for deriving a sorting order which is used to determine the order of the characteristic deviation values of the input pattern.

11. The method according to claim 10 characterized in that the peak amplitude property is selected as the sorting property.

12. A system for nucleic acid sequence point mutation analysis comprising:

means for determining deviations between at least one set of intensity signals representing nucleotide bases in a sample nucleic acid sequence with at least one set of intensity signals from a corresponding reference sequence of predetermined nucleotide composition by comparing said intensity signals at at least one specific nucleotide position, and means for analyzing said deviations to determine the mutation status of said specific nucleotide position in said sample sequence, characterized in that said analyzing means comprises a neural network for generating said mutation status classification based on said deviations, said neural network being trainable on input signals representing deviations based on sample nucleic acid sequences of predetermined mutation status.

13. The system according to claim 12, characterized in that it further comprises an input pattern calculating unit, for transforming, for at least one nucleotide position, raw data signals and nucleotide base sequences of at least one nucleic acid sample sequence and at least one reference sequence, respectively, into deviation values, for determining a base type sorting order, for using said sorting order to assign values to an input pattern for each analyzed nucleotide position, and for outputting said input pattern, a neural network unit, for generating, in response to said input pattern, a neural network output signal, and a mutation status interpreting unit for interpreting said neural network output signal as representing one of at least two mutation classes, whereby at least one of said mutation classes indicates the presence of a mutated nucleotide position.

14. The system of claim 11 or 12, characterized in that it further comprises means for calculating a mutation classification confidence estimate.

15. A program storage device readable by a machine and encoding a program of instructions for executing the steps of the method as defined in claim 1.

* * * * *

UNITED STATES PATENT AND TRADEMARK OFFICE
CERTIFICATE OF CORRECTION

PATENT NO. : 6,260,034 B1
DATED : July 10, 2001
INVENTOR(S) : Bjorkesten

It is certified that error appears in the above-identified patent and that said Letters Patent is hereby corrected as shown below:

<u>Title page, Item [54] and Column 1, line 1,</u>
Title, insert -- A -- before the word "METHOD"

<u>Column 4,</u>
Line 51, replace "TABEL" with -- TABLE --

<u>Column 12,</u>
Line 24, replace "the mutation" with -- The mutation --

<u>Column 14,</u>
Line 17, replace "position," with -- position; --

Signed and Sealed this

Tenth Day of September, 2002

Attest:

JAMES E. ROGAN
Attesting Officer
Director of the United States Patent and Trademark Office

SEQUENCE LISTING

```
<160> NUMBER OF SEQ ID NOS:    1

<210> SEQ ID NO 1
<211> LENGTH: 10
<212> TYPE: DNA
<213> ORGANISM: Homo sapiens

<400> SEQUENCE: 1
cctgaagctc                                                          10
```